US008813281B2

(12) United States Patent
Driemel et al.

(10) Patent No.: US 8,813,281 B2
(45) Date of Patent: Aug. 26, 2014

(54) MEDICAL IMAGING DEVICE

(71) Applicant: Siemens Aktiengesellschaft, Munich (DE)

(72) Inventors: Daniel Driemel, Oederan (DE); Stephan Zink, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/625,169

(22) Filed: Sep. 24, 2012

(65) Prior Publication Data

US 2013/0074263 A1 Mar. 28, 2013

(30) Foreign Application Priority Data

Sep. 26, 2011 (DE) .................. 10 2011 083 381

(51) Int. Cl.
  *A47B 13/00* (2006.01)
  *H05G 1/00* (2006.01)
  *A61B 6/04* (2006.01)
  *A61B 5/05* (2006.01)

(52) U.S. Cl.
  USPC ............. 5/601; 378/208; 378/209; 600/415

(58) Field of Classification Search
  CPC .... A61B 6/0442; A61B 5/055; A61B 6/0407; A61B 2019/5236; A61B 2019/5454; A61B 19/0271; A61G 2210/50; A61N 2005/1055; G01R 33/56375

USPC .................. 5/601; 378/208, 209; 600/415
See application file for complete search history.

(56) References Cited

U.S. PATENT DOCUMENTS

| | | | |
|---|---|---|---|
| 4,567,894 A | | 2/1986 | Bergman |
| 4,727,328 A | | 2/1988 | Carper |
| 4,771,785 A | * | 9/1988 | Duer ............................ 600/415 |
| 5,398,686 A | * | 3/1995 | Inoue et al. .................. 600/415 |
| 5,499,415 A | * | 3/1996 | McKenna ........................ 5/601 |
| 5,619,763 A | * | 4/1997 | Randolph et al. ................. 5/601 |
| 6,044,504 A | * | 4/2000 | Stark ................................ 5/601 |
| 6,459,923 B1 | * | 10/2002 | Plewes et al. ................. 600/411 |
| 6,637,056 B1 | * | 10/2003 | Tybinkowski et al. ........... 5/611 |
| 6,955,464 B1 | * | 10/2005 | Tybinkowski et al. ........ 378/209 |
| 6,973,689 B2 | * | 12/2005 | Lenting et al. .................... 5/601 |
| 7,970,452 B2 | * | 6/2011 | Piron et al. ................... 600/411 |
| 2005/0020906 A1 | * | 1/2005 | Seijger et al. ................ 600/415 |
| 2007/0016003 A1 | * | 1/2007 | Piron et al. .................. 600/415 |
| 2009/0306495 A1 | | 12/2009 | Scarth |

FOREIGN PATENT DOCUMENTS

| | | |
|---|---|---|
| DE | 102004050385 A1 | 5/2006 |
| DE | 102006022297 A1 | 5/2007 |
| JP | 11113881 A | 4/1999 |

* cited by examiner

*Primary Examiner* — William Kelleher
*Assistant Examiner* — Eric Kurilla

(57) ABSTRACT

A medical imaging device is provided. The medical imaging device has a detector unit, a receiving area for receiving a patient for the purposes of a medical imaging examination, and a patient table. The receiving area is cylindrically surrounded by the detector unit. The medical imaging device has at least one deposit unit which can be attached to the patient table.

12 Claims, 6 Drawing Sheets

MEDICAL IMAGING DEVICE

CROSS REFERENCE TO RELATED APPLICATIONS

This application claims priority of German application No. 10 2011 083 381.1 filed Sep. 26, 2011, which is incorporated by reference herein in its entirety.

FIELD OF INVENTION

The present application relates to a medical imaging device comprising a detector unit, a receiving area for receiving a patient for the purposes of a medical imaging examination, the receiving area being cylindrically surrounded by the detector unit, and a patient table.

BACKGROUND OF INVENTION

For medical imaging examinations, such as magnetic resonance scans for example, a patient is conveyed by a patient table into a receiving area of a medical imaging device, the receiving area being cylindrically surrounded by a detector unit, for example a magnet unit, of the medical imaging device. For said medical imaging examinations the patient is prepared on the patient table by a member of the operating staff; for example, the patient is positioned for this purpose on support aids and/or additional local coils are positioned around the patient when magnetic resonance examinations are performed, etc. It can happen in this situation that objects are deposited in the receiving area for temporary storage. If the patient table is subsequently introduced into the receiving area, the objects stored there can lead to undesirable collisions with the patient table. Undesirable damage to the objects and/or to the patient table is also not ruled out. Furthermore, the objects placed within the receiving area can be pushed through the receiving area by the patient table, with the result that said objects can fall down after reaching an end of the receiving area, which can in turn lead to damage to said objects.

SUMMARY OF INVENTION

The object underlying the present application is to provide a medical imaging device with a space-saving deposit unit on the patient table. The object is achieved by the features of the independent claim. Embodiments are described in the dependent claims.

The application proceeds on the basis of a medical imaging device, comprising a detector unit, a receiving area for receiving a patient for the purposes of a medical imaging examination, the receiving area being cylindrically surrounded by the detector unit, and a patient table.

It is proposed that the medical imaging device has at least one deposit unit which can be securely attached to the patient table. This enables a system-integrated deposit unit to be provided within the medical imaging device; said deposit unit can be attached directly to the patient table and accordingly be arranged within range of a member of the operating staff standing by the patient table. In this way objects that are required temporarily for a medical imaging examination can be safely stored for a time without being exposed to a risk of a collision with the patient table and/or damage. Furthermore, owing to a removable arrangement and/or attachment of the deposit unit on the patient table, the patient table can also be used without the deposit unit, such as when the patient is being transported before or after the medical imaging examination for example. In this connection "attachable" is to be understood to mean that the deposit unit is arranged removably on the patient table, in which case neither the deposit unit nor the patient table will forfeit its functionality as a result of the removal of the deposit unit or a releasing of an attachment between the patient table and the deposit unit. The medical imaging device is formed by a magnetic resonance device. As an alternative hereto, an embodiment as a CT device, etc. is also conceivable at any time.

It is furthermore proposed that the deposit unit has at least one coupling element by which the deposit unit can be coupled to the patient table, thereby enabling a constructionally simple mounting and/or attachment and release of the deposit unit on the patient table to be achieved.

If the at least one coupling element of the deposit unit is embodied at least partially as U-shaped, a constructionally simple attachment and/or coupling of the deposit unit to the patient table can be achieved. The deposit unit is attached and/or coupled to the patient table without the use of tools. The coupling element embodied in a U shape has an opening which is configured for receiving a corresponding coupling element. Alternatively hereto the coupling element of the deposit unit can also be formed by a latching element, such as a latching edge for example, such that the deposit units can be released from the patient table only by application of a latching force.

In a development of the application it is proposed that the patient table has at least one coupling element corresponding to the at least one coupling element of the deposit unit and arranged at a front section and/or rear section of the patient table. In this case it is possible to realize a space-saving arrangement on the patient table in which an obstruction of a movement to introduce the patient table into the receiving area and/or a movement within the receiving area is prevented. In this context a front section of the patient table is to be understood to mean a section of the patient table which is formed by an end section pointing in the direction of a movement to introduce the patient table into the receiving area. In this context a rear section of the patient table is to be understood to mean a section of the patient table which is formed by an end section pointing in a direction opposite to a movement to introduce the patient table into the receiving area.

A simple, yet effective coupling element can be realized if the at least one coupling element of the patient table is formed by a wall of the front section and/or the rear section of the patient table. Furthermore the coupling element can be arranged and/or integrated in a cost-effective and space-saving manner within the patient table.

A space-saving arrangement of the deposit unit can furthermore be achieved if the deposit unit is movably mounted within the receiving area. In this case, however, the deposit unit is coupled to the patient table to allow a movement within the receiving area such that in this case objects, such as support aids for the patient on the patient table for example, can be temporarily stored on the deposit unit without in the process being damaged during a movement of the patient table within the receiving area. Moreover, the coupling of the deposit unit to the patient table also prevents the deposit unit and/or objects stored on the deposit unit from falling down.

In a further embodiment of the application it is proposed that the medical imaging device has a guide unit which is disposed within the receiving area for the purpose of guiding the patient table and that the deposit unit is mounted on the guide unit. In this case the deposit unit can be integrated for storage purposes in a space-saving manner in already existing units and/or systems within the receiving area, such as in a guide section of the patient table within the receiving area for example. The guide unit is integrated into a wall of a housing unit surrounding the receiving area.

It is furthermore proposed that the deposit unit has at least one fixing element by which the deposit unit is fixed on the guide unit in a position decoupled from the patient table. The deposit unit can be mounted in a space-saving manner in a position decoupled from the patient table within the receiving area and/or within the guide unit. This also enables the deposit unit to be arranged in a state of permanent readiness and safe against loss within the medical imaging device so that fast access to the deposit unit by a member of the operating staff is possible at all times. The guide unit also has for this purpose at least one fixing element corresponding to the at least one fixing element of the deposit unit. The fixing element of the deposit unit can be formed for example by a recess, such as a groove and/or a borehole, and the second fixing element can be formed by an elevation, such as a ridge, etc. Other embodiments of the two fixing elements that appear to the person skilled in the art as beneficial are also possible at any time.

In addition it is proposed that the fixing element of the guide unit is arranged at an end section facing toward an introduction opening of the receiving area. This enables the deposit unit to be fixed in a position decoupled from the patient table within the receiving area and/or the guide unit in such a way that at least the coupling element of the deposit unit can project from the receiving area and consequently the deposit unit can already be mounted and/or arranged in a correct position for coupling to the patient table within the guide unit.

It is furthermore proposed that prior to an introduction movement along a direction of movement within the guide unit the patient table executes a lifting movement, the lifting movement being substantially vertical with respect to the introduction movement, and during said lifting movement the patient table couples to the deposit unit. In this case the deposit unit can be coupled to the patient table while saving on additional assembly steps and/or additional assembly time.

In a development of the application it is proposed that the deposit unit has a base area on which the fixing element of the deposit unit is arranged, and in an introduction position of the patient table said base area is mounted contactlessly with respect to the guide unit. A fixing and/or securing between the deposit unit and the guide unit in a position of the deposit unit coupled to the patient table can be released. Furthermore the deposit unit together with the patient table can in this way be mounted so as to be movable along a guiding direction within the receiving area and/or within the guide unit.

It is proposed in addition that the medical imaging device has two deposit units and two coupling units, a first deposit unit being coupled to a first end section of the patient table by a first coupling unit and a second deposit unit being coupled to a second end section of the patient table by a second coupling unit. In this arrangement two storage areas can be present on the patient table and can be arranged at opposite end sections of the patient table, such as at a head section and at a foot section of the patient or, more specifically, the patient table for example. Thus, for example, a headset and other objects intended for a head examination can be stored in the first deposit unit at the head section. In contrast, other objects which are necessary for example for a magnetic resonance measurement and which are required following an interruption of the measurement can be stored in a space-saving manner in the second deposit unit. These objects can be used without need for a change in position of the patient within the receiving area, since during the magnetic resonance measurement for example the second deposit unit always projects out of the receiving area and is accessible at all times to the operating staff.

If the deposit unit has at least one storage tray, a safe storage area can be achieved in which the objects stored on the storage tray are secured against falling down.

BRIEF DESCRIPTION OF THE DRAWINGS

Features and details of the application will emerge from the embodiments described herein below as well as with reference to the drawings, in which.

DETAILED DESCRIPTION OF INVENTION

Figure 1:
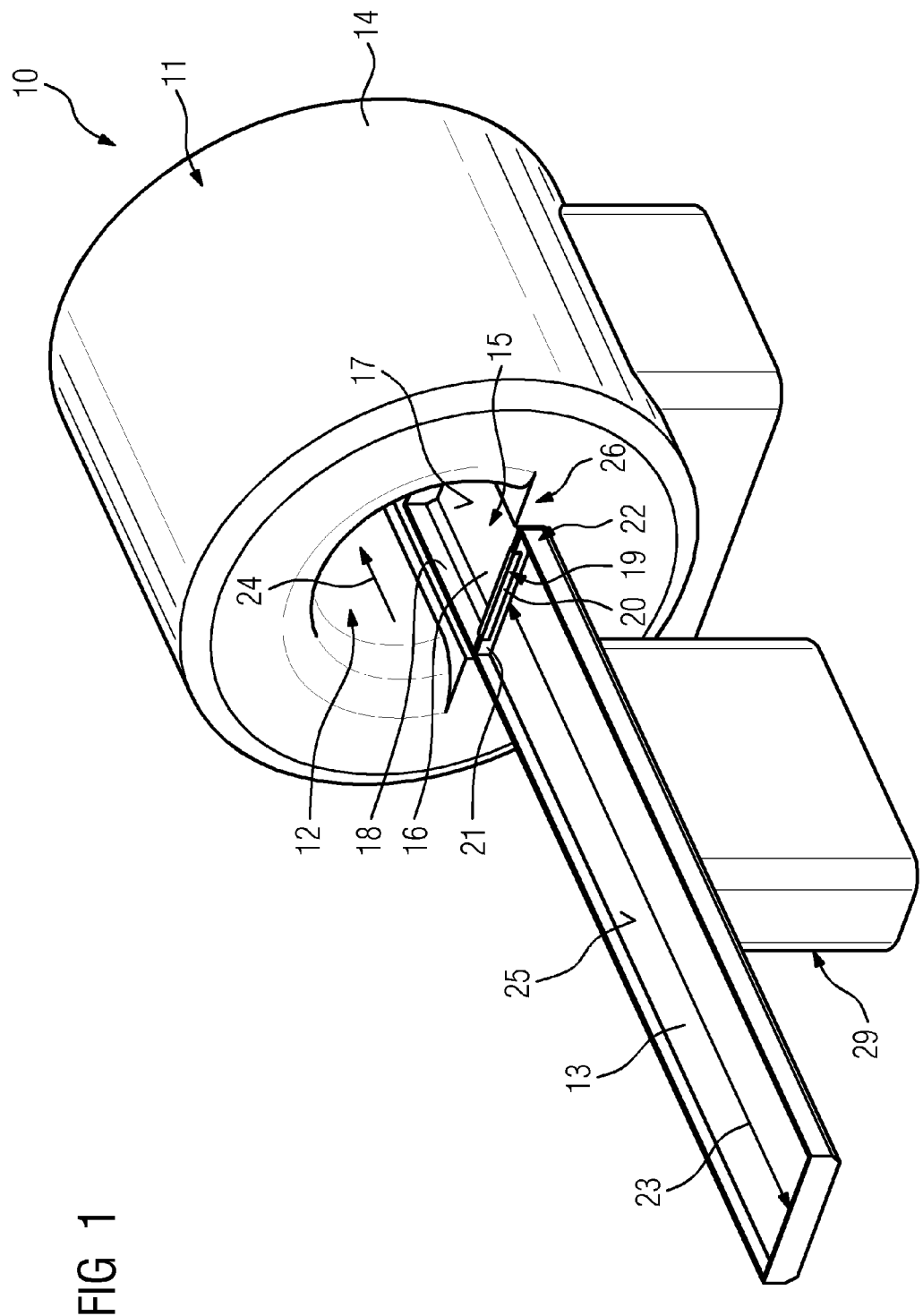
FIG. 1 shows a magnetic resonance device with a patient table and a deposit unit in a schematic view.
Figure 2:
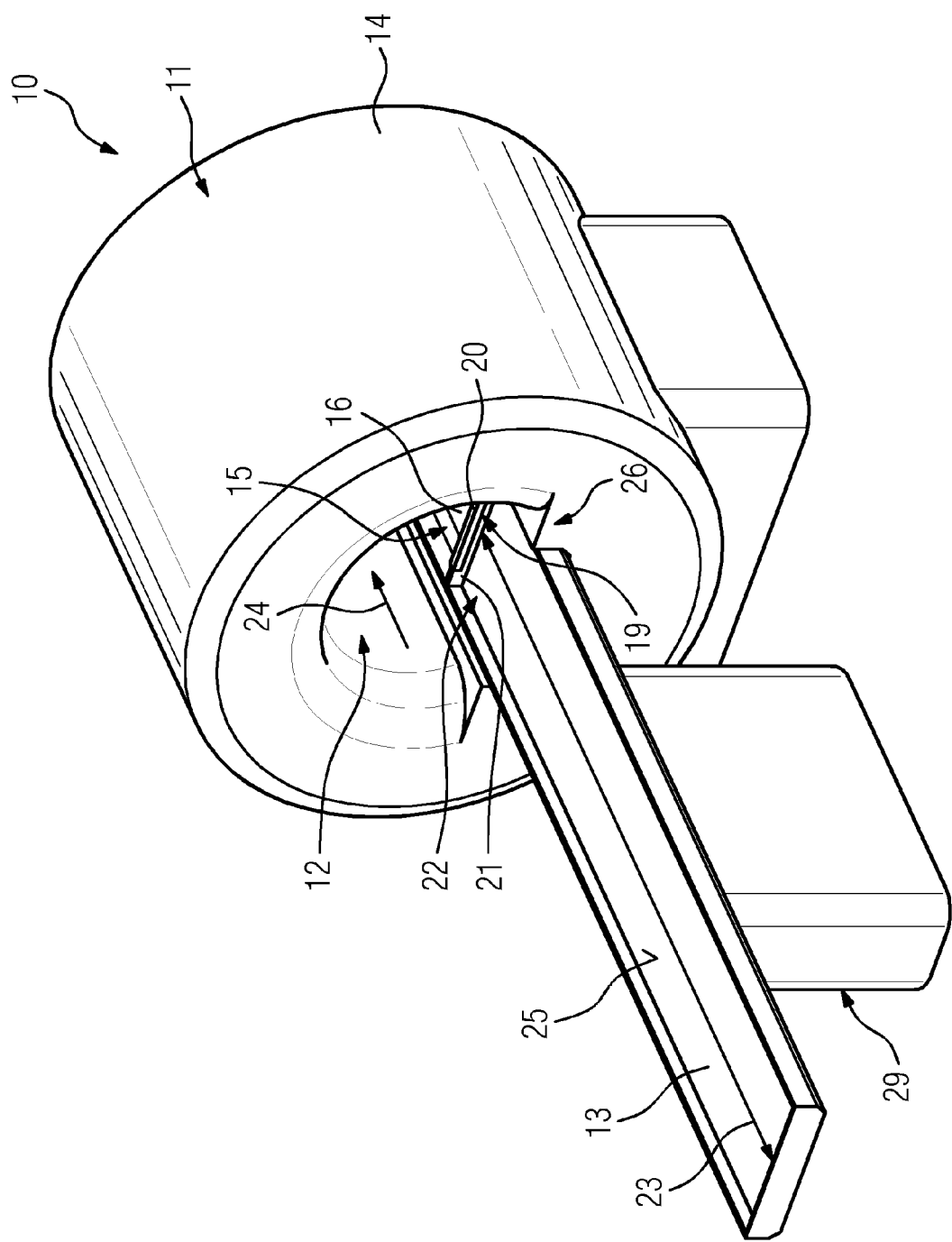
FIG. 2 shows the patient table with the deposit unit coupled to the patient table in a second view.

FIGS. 1 to 6 show schematic views of a medical imaging device 10 according to the application. The medical imaging device 10 is formed by way of example by a magnetic resonance device. Alternatively hereto, the medical imaging device 10 can also be formed by a CT device and/or other medical imaging devices 10 appearing to the person skilled in the art as beneficial.

The magnetic resonance device comprises a detector unit 11 formed by a magnet unit and having a main magnet for generating a strong and constant main magnetic field. The magnetic resonance device also has a cylinder-shaped receiving area 12 for receiving a patient, the receiving area 12 being enclosed by the magnet unit in a circumferential direction. The patient can be introduced into the receiving area 12 by a patient table 13 of the magnetic resonance device. For this purpose the patient table 13 is arranged so as to be movable within the magnetic resonance device. In addition the magnetic resonance device has a housing unit 14 surrounding the magnet unit.

The magnet unit additionally has a gradient coil (not shown in further detail) for generating magnetic field gradients which is used for spatial encoding during an imaging session. The magnet unit also has a radio-frequency coil unit (not shown in further detail) for stimulating a polarization which becomes established in the main magnetic field generated by the main magnet.

In addition the magnetic resonance device has a deposit unit 15 which can be attached to the patient table 13, as shown in FIGS. 1 to 5, representing a first embodiment of the magnetic resonance device with a deposit unit 15. The deposit unit 15 is configured for the purpose of providing a storage area for temporarily storing objects which are required for example for sections of a magnetic resonance examination and which for the remainder of the time of the magnetic resonance examination can be stored on the deposit unit 15. Said objects can include for example a headset and/or support aids, for example for supporting an arm of the patient, and/or local coils and/or an injection unit, etc. The deposit unit 15 comprises a storage tray 16 which has a storage area 17 for storing the objects. In order to provide safe and secure storage of the objects, the storage area 17 is surrounded by a border strip 18 which is oriented substantially vertically with respect to the storage area 17.

In order to attach the deposit unit 15 to the patient table 13 and to detach the deposit unit 15 from the patient table 13, the magnetic resonance device has a coupling unit 19 (FIGS. 1 to 4). The coupling unit 19 comprises two coupling elements 20, 21, a first coupling element 20 being encompassed by the deposit unit 15 and a second coupling element 21 being encompassed by the patient table 13. The coupling element 20 of the deposit unit 15 is formed by a latching edge. In this case the latching edge is formed by an embodiment of an edge of the deposit unit 15 which is at least partially embodied as a latching element and/or at which latching elements that are not shown in further detail are arranged.

The latching edge is arranged on the border strip 18 of the storage tray 16, the latching edge being arranged on a side of the border strip 18 facing away from the storage tray 16. In addition the latching edge together with the border strip 18 has a U-shaped cross-section, an opening of a U-shaped receiving area of the coupling element 20 pointing in a direction which is oriented opposite to a direction of an opening of the storage tray (refer also to FIGS. 3 to 5).

The coupling element 21 of the patient table 13 is embodied in a corresponding manner to the coupling element 20 of the deposit unit 15, such that when they interlock the two coupling elements 20, 21 engage in a connection and in that way the deposit unit 15 is coupled to the patient table 13 or attached to the patient table 13. In this case the coupling element 21 of the patient table 13 is arranged at a front section 22 of the patient table 13, the front section 22 being formed by an end section along a longitudinal extension 23 of the patient table 13 which is disposed at the patient table 13 in a direction of a movement 24 to introduce the patient table 13 into the receiving area 12 and/or which is provided for supporting a head of the patient.

The coupling element 21 of the patient table 13 is formed by a wall of the front section 22 of the patient table 13, the wall having a thickness which is less than an opening width of the coupling element 20 of the deposit unit 15, such that said two coupling elements 20, 21 of the coupling unit 19 can interlock with one another in order to provide a coupling of the deposit unit 15 to the patient table 13. The coupling element 21 or the wall of the patient table 13 is oriented substantially vertically with respect to a reclining surface 25 of the patient table 13, the wall extending away from the reclining surface 25 (FIGS. 3 and 4).

Figure 3:
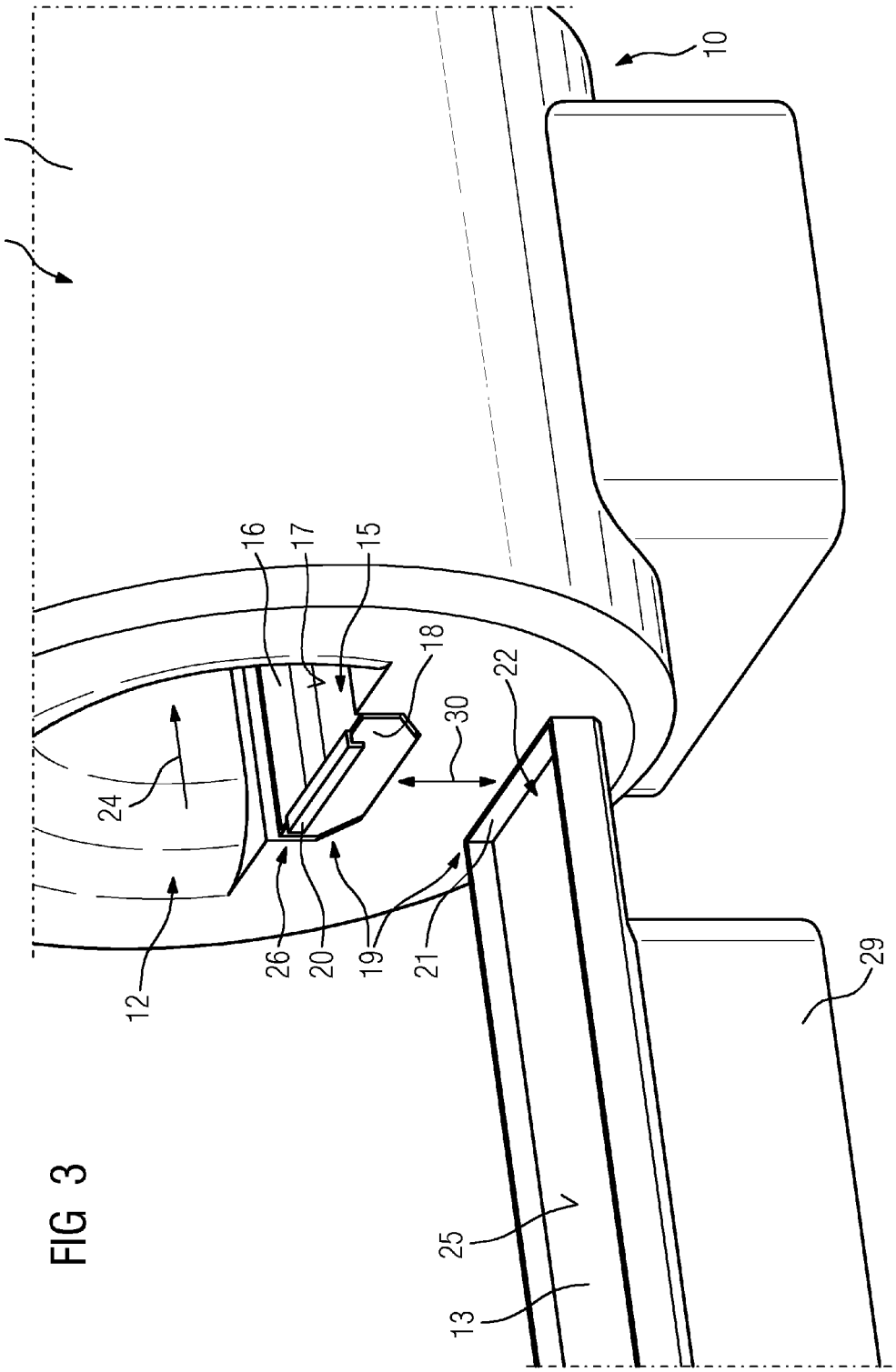
FIG. 3 shows the magnetic resonance device with the deposit unit decoupled from the patient table and the patient table.

In a position decoupled from the patient table 13 the deposit unit 15 is arranged and/or mounted within the receiving area 12 (FIG. 3). In this case the deposit unit 15 is mounted in a guide unit 26 of the magnetic resonance device which is arranged within the receiving area 12 for the purpose of guiding the patient table 13. The guide unit 26 is in this case arranged in a subsection of the housing units 14 cylindrically surrounding the receiving area 12. The deposit unit 15 is furthermore mounted at an end section of the guide unit 26 facing the introduction opening, the deposit unit 15 facing the introduction opening with the side having the coupling element 20.

Figure 4:
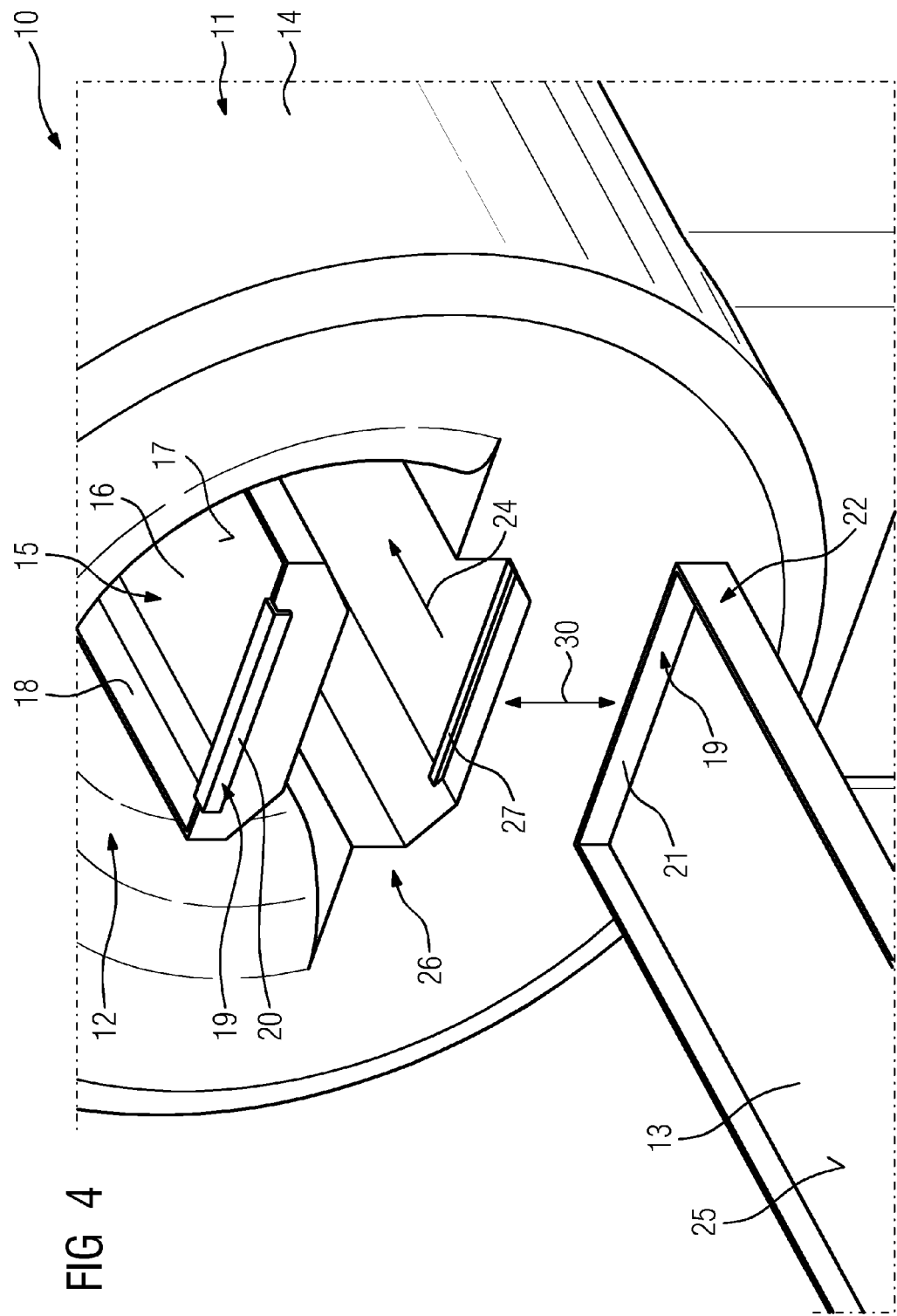
FIG. 4 shows a first view of the guide unit with raised deposit unit.

In order to ensure a secure mounting of the deposit unit 15 within the guide unit 26, the guide unit 26 has a fixing element 27 (FIG. 4). The fixing element 27 is formed by an elongate elevation which is arranged on the guide unit 26. In this case the fixing element 27 extends in a direction that is substantially vertical with respect to a guiding direction of the guide unit 26, the guiding direction being aligned parallel to the movement direction 24. The fixing element 27 is in this case arranged at an end section of the guide unit 26 facing the introduction opening of the receiving area 12.

Figure 5:
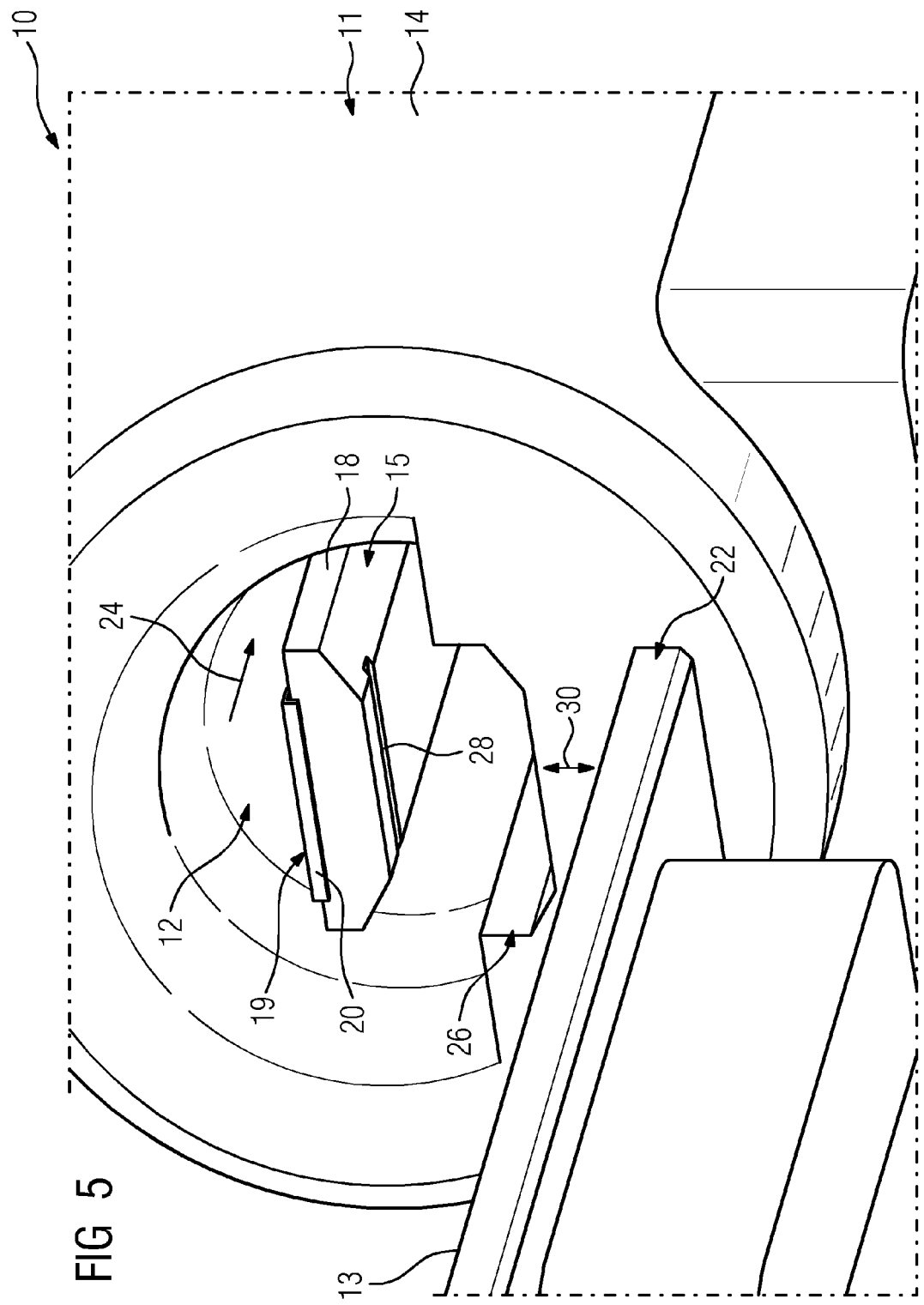
FIG. 5 shows a second view of the guide unit with raised deposit unit.

Furthermore, the deposit unit 15 also has a fixing element 28 which is embodied in a corresponding manner to the fixing element 17 of the guide unit 13 (FIG. 5). In the present embodiment the fixing element 28 of the deposit unit 15 is formed by a groove embodied as oblong and arranged at a base area of the deposit unit 15 facing away from the storage area 17 or at a side of the deposit unit 15 facing in a mounting position of the guide unit 26.

The two fixing elements 27, 28 are arranged on the guide unit 26 and on the deposit unit 15 in such a way that the fixing element 27 of the guide unit 26 engages with the fixing element 28 of the deposit unit 15 in a mounting position of the deposit unit 15 and in so doing secures the deposit unit 15 against a movement within the guide unit 26. Furthermore, in the mounting position of the deposit unit 15 the latter is arranged within the guide unit 26 in such a way that the coupling element 20 of the deposit unit 15 projects out of the guide unit 26 at the end facing toward the introduction opening. Moreover, the coupling element 20 arranged on the deposit unit 15 also projects beyond the housing unit 14 surrounding the magnet unit 11. In contrast, the deposit unit 15 together with the storage tray 16 and the wall 18 bordering the storage tray 16 is arranged within the guide unit 26 and the receiving area 12.

In order to effect a coupling between the deposit unit 15 and the patient table 13, the patient table 13 is first driven up to the magnet unit 11. For this purpose the patient table 13 has a carriage 29 which is only indicated schematically in FIGS. 1 to 5. As soon as the patient table 13 bears against the magnet unit 11 with the front section 22, the patient table 13 is raised by a lifting movement 30 to a level of the introduction opening (FIG. 3). During said lifting movement 30 the coupling element 21 arranged on the wall of the patient table 13 engages in the U-shaped coupling element 20 of the deposit unit 15 such that the deposit unit 15 is coupled to the guide unit 13.

The two coupling elements 20, 21 are furthermore dimensioned such that in an introduction position the patient table 13 raises the deposit unit 15 coupled to the patient table 13 such that the fixing of the deposit unit 15 to the guide unit 26 is canceled and/or released. As a result of said raising of the deposit unit 15, the base area of the deposit unit 15 is mounted contactlessly with respect to the guide unit 26. By this means the deposit unit 15 together with patient table 13 is movably mounted within the receiving area 12, such as the guide unit 26, the deposit unit 15 being coupled to the patient table 13 to allow a movement within the receiving area 12 and/or the guide unit 16.

In order to release the deposit unit 15 from the patient table 13, the patient table 13 is first moved out of the receiving area 12. In this position the patient table 13 is disposed along the guiding direction outside of the guide unit 26 and the receiving area 12. The deposit unit 15, in contrast, is still disposed in the guiding direction within the receiving area 12, the coupling element 20 likewise being disposed in the guiding direction outside of the receiving area 12 and outside of the guide unit 26. In this position of the deposit unit 26 and the patient table 13, the patient table 13 is lowered, a direction of said lifting movement 30 formed by a lowering movement being substantially vertical with respect to the guiding movement of the patient table 13. Said lowering movement initially causes the deposit unit 15 to be lowered as well until the base area comes into contact with the guide unit 26 and in addition the two fixing elements 27, 28 interlock. Furthermore, the coupling between the deposit unit 15 and the patient table 13 is also released and/or canceled as a result of the lowering movement.

Figure 6:
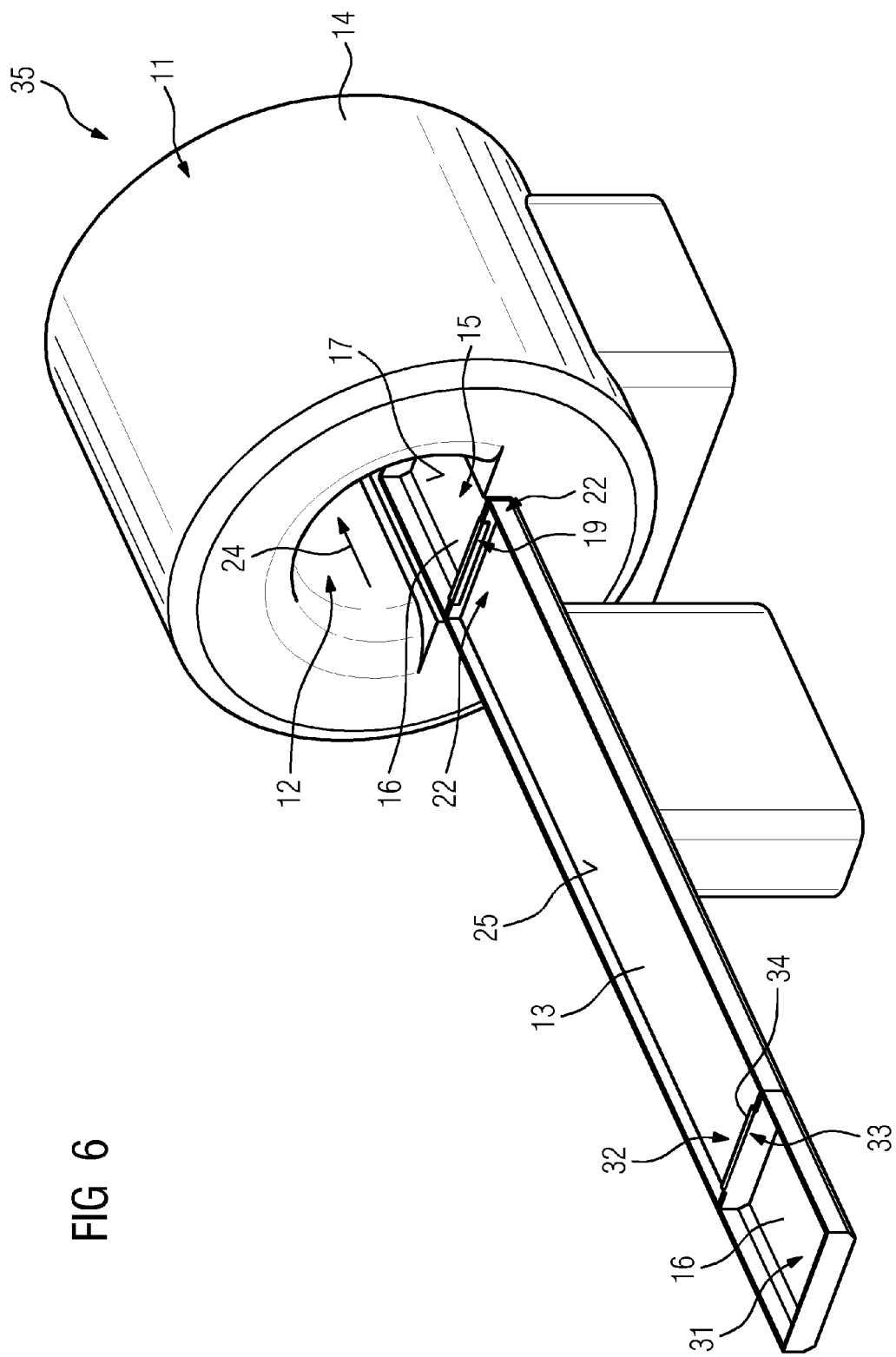
FIG. 6 shows a magnetic resonance device embodied alternatively to FIGS. 1 to 5, with two deposit units.

An alternative embodiment of a medical imaging device 35 is illustrated in FIG. 6. Components, features and functions remaining substantially the same are basically labeled with the same reference numerals. The following description is limited to the differences from the embodiment shown in FIGS. 2 to 5, with reference being made to the description of the embodiment shown in FIGS. 2 to 5 in respect of components, features and functions remaining the same.

The medical imaging device 35 depicted in FIG. 6 is formed by a magnetic resonance device and has two deposit units 15, 31. A first of the two deposit units 15 can be coupled to the patient table 13 at a front section 22 of the patient table 13 and a second of the two deposit units 31 can be coupled to the patient table 13 at a rear section 32 of the patient table 13. For this purpose the magnetic resonance device has two coupling units 19, 33, a first coupling unit 19 being configured for coupling the first deposit unit 15 to a first end section of the patient table 13 and a second coupling unit 33 being configured for coupling the second deposit unit 31 to a second end section of the patient table 13. The first end section is formed by the front section 22 and the second end section by the rear section 32 of the patient table 13.

The front section 22 of the patient table 13 and the first deposit unit 15 are embodied analogously to the description relating to the embodiment depicted in FIGS. 2 to 5. The second deposit unit 31 is removably arranged at the rear section 32 of the patient table 13. In this case the second deposit unit 31 can be arranged for coupling to the patient table 13 by a member of the operating staff at the patient table 13. Alternatively to the embodiment presented in FIG. 6, the second deposit unit 31 can also be arranged permanently, undetachably, on the patient table 13.

The second deposit unit 31 is embodied analogously to the first deposit unit 15 for reasons of cost. In principle, however, an embodiment of the second deposit unit 31 differing from the embodiment of the first deposit unit 15 is also conceivable at any time, such as an embodiment of the second deposit unit 31 in which one fixing element is dispensed with, for example.

With regard to an arrangement and/or embodiment with a coupling element 34 of the second coupling unit 33, the rear section 32 of the patient table 13 is embodied analogously to the front section 22 and an arrangement of a coupling element 21 of the first coupling unit 19 at the front section 22 of the patient table 13.

Alternatively to the two embodiments shown, it may also be possible in an alternative embodiment of the application for the magnetic resonance device to have a single deposit unit 31 which is arranged at the rear section 32 of the patient table 13.

The invention claimed is:

1. A medical imaging device, comprising: a detector unit; a receiving area cylindrically surrounded by the detector unit for receiving a patient for a medical imaging examination; a patient table; a first deposit unit that can be attached to the patient table, wherein the first deposit unit comprises a first coupling element by which the first deposit unit can be coupled to the patient table; and a second deposit unit comprising a second coupling element, wherein the first deposit unit couples to a first end section of the patient table by the first coupling element, and wherein the second deposit unit couples to a second end section of the patient table by the second coupling element, wherein the deposit units comprises at least one storage tray for storing objects that are required for a magnetic resonance examination, and wherein the storage tray comprises a storage area surrounded by a border strip, and wherein the first deposit unit and the second deposit unit are identical.

2. The medical imaging device as claimed in claim 1, wherein the first and/or second coupling element of the deposit units is at least partially U-shaped.

3. The medical imaging device as claimed in claim 1, wherein the patient table comprises a coupling element corresponding to the first and/or second coupling element of the deposit units and is arranged at a front section and/or rear section of the patient table.

4. The medical imaging device as claimed in claim 3, wherein the coupling element of the patient table is formed by a wall of the front section and/or of the rear section of the patient table.

5. The medical imaging device as claimed in claim 1, wherein the first and/or the second deposit unit is movably mounted within the receiving area.

6. The medical imaging device as claimed in claim 1, wherein the first and/or the second deposit unit is coupled to the patient table to allow a movement within the receiving area.

7. The medical imaging device as claimed in claim 1, further comprising a guide unit that is arranged within the receiving area for guiding the patient table, and wherein the first and/or the second deposit unit is mounted on the guide unit.

8. The medical imaging device as claimed in claim 7, wherein the first and/or the second deposit unit comprises a fixing element by which the deposit unit is fixed to the guide unit in a position decoupled from the patient table.

9. The medical imaging device as claimed in claim 8, wherein the guide unit comprises a fixing element corresponding to the fixing element of the first and/or the second deposit unit.

10. The medical imaging device as claimed in claim 9, wherein the fixing element of the guide unit is arranged at an end section facing toward an introduction opening of the receiving area.

11. The medical imaging device as claimed in claim 8, wherein the patient table is configured to execute a lifting movement prior to an introduction movement along a direction within the guide unit, wherein the lifting movement is vertical with respect to the introduction movement, and wherein the patient table couples to the first and/or the second deposit unit during the lifting movement.

12. The medical imaging device as claimed in claim 11, wherein the first and/or the second deposit unit comprises a base area at which the fixing element of the first and/or the second deposit unit is arranged, and wherein the base area is mounted indirectly to the guide unit in the introduction movement of the patient table.

* * * * *